United States Patent
Van De Graaf et al.

(10) Patent No.: US 7,265,239 B2
(45) Date of Patent: Sep. 4, 2007

(54) PROCESS FOR THE CONVERSION OF FURFURYL ALCOHOL INTO LEVULINIC ACID OR ALKYL LEVULINATE

(75) Inventors: Wouter David Van De Graaf, Amsterdam (NL); Jean-Paul Lange, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 11/466,630

(22) Filed: Aug. 23, 2006

(65) Prior Publication Data

US 2007/0049771 A1   Mar. 1, 2007

(30) Foreign Application Priority Data

Aug. 26, 2005 (EP) ................................. 05107824

(51) Int. Cl.
*C07C 69/66* (2006.01)
*C07C 59/00* (2006.01)

(52) U.S. Cl. ...................................... 560/174; 562/577
(58) Field of Classification Search ..................... None
See application file for complete search history.

(56) References Cited

U.S. PATENT DOCUMENTS

| 2,738,367 A | 3/1956 | Redmon ..................... 260/528 |
| 4,236,021 A | 11/1980 | Hsu et al. ................... 560/174 |
| 5,175,358 A | 12/1992 | Capai et al. ................ 562/537 |
| 2003/0140711 A1 | 7/2003 | Brown ..................... 73/861.95 |

FOREIGN PATENT DOCUMENTS

| WO | 95/19222 | 7/1995 |
| WO | 96/19288 | 6/1996 |

*Primary Examiner*—Sikarl A. Witherspoon

(57) ABSTRACT

A process for the conversion of furfuryl alcohol into levulinic acid or alkyl levulinate comprising contacting furfuryl alcohol and water or an alkyl alcohol with a porous heterogeneous catalyst comprising strong acid ion-exchange resin, wherein the catalyst has pores with an average pore diameter in the range of from 1 to 1000 nm.

20 Claims, No Drawings

PROCESS FOR THE CONVERSION OF FURFURYL ALCOHOL INTO LEVULINIC ACID OR ALKYL LEVULINATE

CROSS-REFERENCE TO RELATED APPLICATION

This application claims priority from European Patent Application No. 05107824.4, filed on Aug. 26, 2005, which is incorporated herein by reference.

FIELD OF THE INVENTION

The present invention provides a process for the conversion of furfuryl alcohol into levulinic acid or alkyl levulinate.

BACKGROUND OF THE INVENTION

It is known that furfuryl alcohol can be converted into levulinic acid or alkyl levulinate by reacting furfuryl alcohol and water or an alkyl alcohol in the presence of a homogeneous strong acidic catalyst. In U.S. Pat. No. 4,236,021, for example, is disclosed the esterification of furfuryl alcohol with a different alcohol in the presence of a strong acid catalyst such as hydrogen chloride, hydrogen bromide or oxalic acid. In U.S. Pat. No. 5,175,358 is disclosed the production of levulinic acid by heating and ring-opening furfuryl alcohol in the presence of water and a strong non-oxidising protonic acid, wherein the furfuryl alcohol is progressively introduced into a mixture of water, the strong protonic acid and an amount of levulinic acid that serves as the reaction solvent. Hydrochloric acid, hydrobromic acid, hydroiodic acid, sulphuric acid, pyrosulphuric acid, perchloric acid, the phenylsulphonic acids, methanesulphonic acid, chlorosulphonic acid and fluorosulphonic acid are mentioned as being exemplary of such strong protonic acids.

In U.S. Pat. No. 2,738,367 is disclosed a process for producing levulinic acid by heating an aqueous solution of furfuryl alcohol at a temperature in the range of from 30 to 100° C. in the presence of a strongly acidic exchange resin as catalyst. The catalysts that are disclosed in U.S. Pat. No. 2,738,367, i.e. the cation exchange resins marketed under the tradenames "Amberlite IR-120" and "Amberlite IR-105", are both gel-type cation exchange resins, i.e. a non-porous form of cation exchange resin.

SUMMARY OF THE INVENTION

It has now been found that if a porous strong acid ion-exchange resin is used as catalyst for the conversion of furfuryl alcohol with water or an alkyl alcohol into levulinic acid or alkyl levulinate, respectively, the reaction can be carried out with a higher selectivity towards levulinic acid or alkyl levulinate than when a non-porous strong acid ion-exchange resin is used.

Accordingly, the present invention provides a process for the conversion of furfuryl alcohol into levulinic acid or alkyl levulinate comprising contacting furfuryl alcohol and water or an alkyl alcohol with a porous heterogeneous catalyst comprising strong acid ion-exchange resin, wherein the catalyst has pores with an average pore diameter in the range of from 1 to 1000 nm.

DETAILED DESCRIPTION OF THE INVENTION

In the process according to the invention, furfuryl alcohol and water are contacted with a porous heterogeneous catalyst comprising strong acid ion-exchange resin in order to convert the furfuryl alcohol into levulinic acid or furfuryl alcohol and alkyl alcohol are contacted with such catalyst in order to convert the furfuryl alcohol into the corresponding alkyl levulinate. Preferably, the conversion reaction is carried out in liquid phase. An advantage of a liquid phase reaction is that liquid by-products that may be formed, such as for example oligomeric condensation products of furfuryl alcohol and/or alkyl levulinate, will be easily removed from the catalyst pores by the liquid reaction medium. Therefore, preferably a liquid reaction mixture comprising furfuryl alcohol and water or alkyl alcohol is contacted with the catalyst.

In order to limit the amount of by-products formed, in particular oligomeric condensation products of furfuryl alcohol, it is preferred to keep the concentration of furfuryl alcohol in the liquid reaction mixture below 10 wt %, preferably below 2 wt %, based on the total weight of the liquid reaction medium. Typically, the concentration of furfuryl alcohol in the liquid reaction mixture is at least 0.001 wt %, preferably at least 0.1 wt %.

A low concentration of furfuryl alcohol may be achieved in several ways. The liquid reaction mixture may for example be diluted with an excess of the other reactant, i.e. alkyl alcohol or water, or with the reaction product, i.e. alkyl levulinate or levulinic acid, or with a diluent not being reactant or reaction product, for example sulpholane, gamma valerolactone or a carboxylate ester. Alternatively or additionally, staged supply of furfuryl alcohol to the reaction mixture or a continuously stirred tank reactor (CSTR) may be applied in order to keep the concentration of furfuryl alcohol sufficiently low.

In order to achieve a high conversion of furfuryl alcohol, water or alkyl alcohol is present in the liquid reaction mixture in at least the stoichiometric amount, more preferably in stoichiometric excess. Therefore, the molar ratio of water and furfuryl alcohol or of alkyl alcohol and furfuryl alcohol in the liquid reaction mixture is preferably in the range of from 1 to 100, more preferably of from 1.5 to 10.

The catalyst used in the process according to the invention is a porous heterogeneous catalyst comprising strong acid ion-exchange resin, the catalyst having pores with an average diameter in the range of from 1 to 1000 nm. The catalyst may be a porous strong acid ion-exchange resin as such, for example a macro-reticular strong acid ion-exchange resin. Alternatively, the catalyst may comprise a non-porous strong acid ion-exchange resin dispersed within a porous structure of refractory oxide, for example a sol-gel derived porous micro-composite of ion-exchange polymer and metal oxide as disclosed in WO 95/19222 or WO 96/19288.

Reference herein to average pore diameter is to the volume averaged pore diameter. The average pore diameter may suitably be determined by means of BET nitrogen adsorption. The catalyst used in the process according to the invention will typically have a mono-modal pore structure, i.e. all pores having a diameter in a single pore diameter range. The catalyst may, however, have a bi-modal pore structure, i.e. having pores in two distinct pore diameter ranges. In that case, the catalyst is characterised by two different average pore diameters, each being in the range of from 1 to 1000 nm.

An ion-exchange resin has an insoluble polymeric matrix containing labile ions capable of exchanging with ions in the surrounding medium. Ion-exchange resins are typically grouped in four general categories, i.e. strong acid, weak acid, strong base and weak base. In the process according to the invention, a strong acid ion-exchange resin is used. Ion-exchange resins with sulphonic or phosphonic ion-exchange groups are for example considered to be strong acid ion-exchange resins, in contrast to ion-exchange resins with carboxylic groups, which are considered to be weak acid ion-exchange resins.

Any strong acid ion-exchange resin may be used. Such ion-exchange resins are known in the art and commercially available. Preferably, the ion-exchange resin used in the process according to the invention has sulphonic or phosphonic groups, more preferably sulphonic groups. Examples of suitable ion-exchange resins are cross-linked polystyrene, polyethene or polysiloxane resins or polymeric perfluororesins.

The catalyst is preferably a macro-reticular ion-exchange resin. Macro-reticular ion-exchange resins are known in the art and comprise two continuous phases, i.e. a continuous pore phase and a continuous polymeric phase. The polymeric phase is structurally composed of small spherical microgel particles agglomerated together to form clusters, which, in turn are fastened together at their interphases and form interconnecting pores. Typically, macro-reticular ion-exchange resins have a specific surface area in the range of from 5 to 1500 $m^2/g$. The surface area arises from the freely exposed surface of the microgel particles. Macro-reticular ion-exchange resins typically have an average pore diameter in the range of from 1 to 1000 nm, usually of from 10 to 100 nm. Macro-reticular ion-exchange resins are to be contrasted with gel-type resins, which do not have permanent pore structures. The non-permanent pores in gel-type ion-exchange resins are usually referred to as gelular pores or molecular pores. For the purpose of this specification, gel-type ion-exchange resins are not considered as porous materials. Reference herein to porous materials is to materials with permanent pores.

It is preferred that the concentration of acidic ion-exchange groups in the resins is at least 1 milli-equivalent $H^+$ per gram dry resin, more preferably at least 3 milli-equivalents $H^+$ per gram dry resin.

Preferably, the catalyst has a specific surface area of at least 5 $m^2/g$, more preferably at least 20 $m^2/g$. Reference herein to specific surface area is to the specific surface area as determined by BET nitrogen adsorption.

In the process according to the invention, the ion-exchange catalyst may be arranged in any suitable form, for example as a fixed bed of particles or as dispersed particles.

The process according to the invention may be carried out as a batch, semi batch or continuous process. If furfuryl alcohol is continuously fed to the catalyst, it is preferred to supply the furfuryl alcohol at a feed rate of at most 20 grams furfuryl alcohol per gram catalyst per hour, more preferably at most 15 g/g/h, even more preferably at most 10/g/g/h.

In one preferred embodiment, the process is carried out in a continuously stirred tank reactor (CSTR) containing liquid reaction mixture and catalyst particles. An advantage of such CSTR reactor is that the furfuryl alcohol that is fed into the reactor is rapidly mixed in the reaction mixture, thus avoiding a high concentration of furfuryl alcohol at the inlet.

The process according to the invention is typically carried out at a temperature above 60° C., preferably at a temperature in the range of from 80 to 250° C., more preferably in the range of from 100 to 220° C. The upper limit depends, inter alia, on the temperature-resistance of the catalyst used. It will be appreciated that in case a styrene-based ion-exchange resin is used as catalyst, the temperature should typically not exceed 150° C. A temperature in the range of from 110 to 150° C. is particularly preferred.

The pressure at which the reactants are contacted with the catalyst is not critical. Preferably, in order to avoid evaporation of reactants, the pressure is at least the autogeneous pressure of the liquid reaction mixture at the temperature at which the conversion reaction is carried out.

Preferably, the process according to the invention is a process for the conversion of furfuryl alcohol into alkyl levulinate by contacting furfuryl alcohol and an alkyl alcohol with a porous heterogeneous acid catalyst. The alkyl alcohol preferably is an alkyl alcohol having at most 10 carbon atoms, more preferably a primary alkyl alcohol having at most 10 carbon atoms, even more preferably methanol, ethanol, 1-butanol, 1-pentanol, 2-ethylhexan-1-ol or a combination of two or more thereof. Ethanol is particularly preferred.

It has been found that, in case the process is a process for the conversion of furfuryl alcohol into alkyl levulinate by reacting furfuryl alcohol with an alcohol having up to four carbon atoms, in particular up to three carbon atoms, the selectivity towards alkyl levulinate increases with an increasing ratio between strong acidic groups on the surface and inside the polymeric phase of the ion exchange resin. Preferably, the ion-exchange resin has a ratio of strong acidic groups at its surface and strong acidic groups inside its polymeric phase that is at least 3.0.

The amount of acidic groups on the surface may suitably be determined by means of X-ray photoelectron spectroscopy (XPS). The amount of acidic groups inside the polymeric phase may suitably be determined by means of X-ray fluorescence spectroscopy (XRF). In the case of sulphonic groups, for example, the ratio between surface and non-surface sulphonic groups can be calculated from the ratio of sulphur atoms at the surface as measured by XPS and sulphur atoms inside the polymeric phase as measured by XRF.

EXAMPLES

The invention is further illustrated by means of the following non-limiting examples.

Example 1

An amount of catalyst and an amount of ethanol were loaded in a 250 mL autoclave reactor. The autoclave was closed and heated to 125° C. A feed mixture consisting of 110 g furfuryl alcohol (36 mole %), 70 g ethanol (63 mole %) and 2 g (0.3 mole %) of n-dodecane as internal standard was continuously fed to the autoclave under continuous stirring (1500 rpm). The temperature was maintained at 125° C. After addition of the whole feed mixture, the reactor was cooled and the liquid reaction mixture was analysed by gas chromatography.

In Table 1 is shown the experimental set-up for each experiment, i.e. the type of catalyst, the amounts of catalyst and ethanol initially loaded in the reactor, the weight hourly velocity at which furfuryl alcohol was fed to the reactor and the duration of the conversion reaction. In Table 1 is also shown the conversion of furfuryl alcohol and the yield of ethyl levulinate (EL). The EL yield is expressed as mole % based on the moles of furfuryl alcohol supplied to the reactor.

In experiments 1 to 13, commercially available ion-exchange resins were used as catalyst. In experiments 1 to 9 strong acid macro-reticular ion-exchange resins were used (according to the invention); in experiments 10 to 13, strong acid gel-type ion-exchange resins were used (not according to the invention). For reference, sulphuric acid was used as catalyst in experiments 14 to 16 (not according to the invention).

In Table 2, the characteristics of the commercially available ion-exchange resin used as catalyst in experiments 1 to 13 are given. All ion-exchange resins used in experiments 1 to 13 are cross-linked polystyrene resins, which are cross-linked with divinylbenzene (DVB), and have acidic sulphonic groups.

From the results, it can be seen that strong acidic macro-reticular ion-exchange resin are suitable catalysts for the conversion of furfuryl alcohol into ethyl levulinate. Macro-reticular ion-exchange resins show a better performance than gel-type ion-exchange resins. Further, a low supply velocity of furfuryl alcohol, resulting in a low concentration of furfuryl alcohol in the reaction mixture, results in a higher conversion of furfuryl alcohol into ethyl levulinate than a high supply velocity of furfuryl alcohol. The effect of furfuryl alcohol concentration on conversion and yield appears to be much stronger for the heterogeneous catalysts (ion-exchange resins in experiments 1 to 13) than for the homogeneous catalysts (sulphuric acid in experiments 14 to 16).

Example 2

Twelve grams of macroreticular strong acid ion-exchange resin and 57 grams ethanol were loaded in a 250 mL autoclave reactor. The autoclave was closed and heated to 125° C. A feed mixture consisting of 90 g furfuryl alcohol (43 mole %), 55 g ethanol (56 mole %) and 1.5 g (0.4 mole %) of n-dodecane as internal standard was continuously fed to the autoclave under continuous stirring (1500 rpm). The temperature was maintained at 125° C. After addition of the whole feed mixture, the reactor was cooled and the liquid reaction mixture was analysed by gas chromatography.

In Table 3 is shown the experimental set-up for each experiment, i.e. the type of catalyst, the ratio between sulphonic acid groups on the surface ($S_{XPS}$) and sulphonic acid groups inside the polymeric phase of the catalyst ($S_{XRF}$), the weight hourly velocity at which furfuryl alcohol was fed to the reactor and the duration of the conversion reaction. In Table 3 is also shown the conversion of furfuryl alcohol, the yield of ethyl levulinate (EL) and the amount of di-ethylether that is formed. The EL yield is expressed as mole % based on the moles of furfuryl alcohol supplied to the reactor and the amount of di-ethylether formed is expressed as mole % based on the moles of ethanol supplied to the reactor.

The results in Table 3 show that the use of a ion-exchange resin with a relatively high concentration of sulphonic groups at the external surface, i.e. with a high $S_{XPS}/S_{XRF}$ ratio, show a low selectivity for the undesirable di-ethylether formation. For instance, at a comparable ethyl levulinate yield, the use of Amberlyst 46 as catalyst ($S_{XPS}/S_{XRF}$ ratio is 4.6) results in a lower di-ethylether yield than the use of the other catalysts (all with a $S_{XPS}/S_{XRF}$ ratio below 3).

TABLE 1

Experimental set-up and results for experiments 1 to 16

| Experiment | catalyst | initial reactor loading (g) catalyst | ethanol | WHV[a] Falc[b] (g/g/h) | time (min) | Falc[b] conversion (mole %) | EL[c] yield (mole %) |
|---|---|---|---|---|---|---|---|
| 1 | Amberlyst 35 | 11.4 | 51.0 | 2.9 | 149 | 99.5 | 91 |
| 2 | idem | 11.4 | 52.7 | 14.0 | 31 | 99.6 | 83 |
| 3 | idem | 4.2 | 55.6 | 41.7 | 31 | 93 | 42 |
| 4 | Amberlyst 15 | 12.0 | 52.0 | 5.8 | 70 | 99.7 | 81 |
| 5 | Idem | 7.2 | 51.8 | 17.4 | 40 | 98.5 | 59 |
| 6 | Amberlyst 36W | 13.5 | 51.8 | 5.3 | 67 | 100 | 77 |
| 7 | Idem | 6.0 | 51.2 | 25.0 | 33 | 95 | 55 |
| 8 | Purolite MN500 | 12.4 | 51.9 | 5.5 | 70 | 100 | 76 |
| 9 | Idem | 4.0 | 52.0 | 23.0 | 53 | 92 | 35 |
| 10 | Dowex 50WX8 | 12.0 | 52.7 | 6.0 | 67 | 99.4 | 51 |
| 11 | Idem | 6.2 | 51.1 | 14.4 | 55 | 66 | 15 |
| 12 | Dowex 50WX4 | 10.3 | 52.8 | 12.7 | 40 | 95 | 37 |
| 13 | Idem | 3.9 | 51.0 | 41.7 | 30 | 91 | 31 |
| 14 | $H_2SO_4$ | 6.3 | 56.2 | 5.8 | 148 | 99.6 | 88 |
| 15 | $H_2SO_4$ | 6.3 | 56.3 | 28.1 | 32 | 99.5 | 83 |
| 16 | $H_2SO_4$ | 2.0 | 56.1 | 88.9 | 30 | 99.3 | 73 |

[a]WHV: weight hourly velocity;
[b]Falc: furfuryl alcohol;
[c]EL: ethyl levulinate.

TABLE 2

Characteristics of ion-exchange resins used in experiments 1 to 13.

| Resin | | acidity | | cross-linking | specific surface | pore diameter |
|---|---|---|---|---|---|---|
| Name | type | meq $H^+$/ml | meq $H^+$/g | (wt % DVB[a]) | area[b] ($m^2/g$) | (nm) |
| Amberlyst 15[d] | MR[c] | 1.7 | 4.70 | 20 | 45 | 25 |
| Amberlyst 35[d] | MR[c] | 1.9 | 5.20 | 20 | 44 | 30 |
| Amberlyst 36W[d] | MR[c] | 2.0 | 5.45 | 12 | 25 | 20 |
| Purolite MN500[e] | MR[c] | | 2.00 | | 908 | 90 |
| Dowex 50 WX4[f] | gel | 1.1 | | 4 | <<1 (gel) | — |
| Dowex 50 WX8[f] | gel | 1.7 | | 8 | <<1 (gel) | — |

[a]DVB: divinylbenzene
[b]as determined by the nitrogen BET method
[c]MR: macro-reticular
[d]ex. Rohm and Haas
[e]ex. Purolite International Limited
[f]ex. Dow Chemical Company

TABLE 3

Experimental set-up and results for experiments 17 to 23

| Experiment | Catalyst | S concentration in catalyst (wt % S) | | | WHV[a] Falc[b] (g/g/h) | time (min) | Falc[b] conversion (mole %) | EL[c] yield (mole %) | DEE[d] yield (mole %) |
|---|---|---|---|---|---|---|---|---|---|
| | | surface $S_{XPS}$ | inside $S_{XRF}$ | ratio $S_{XPS}/S_{XRF}$ | | | | | |
| 17 | Amberlyst 46 | 15.6 | 3.4 | 4.6 | 11.5 | 33 | 97 | 68 | 0.4 |
| 18 | idem | | | | 5.7 | 66 | 100 | 81 | 0.6 |
| 19 | Amberlyst 15 | 16.3 | 7.1 | 2.3 | 5.8 | 70 | 100 | 89 | 4.0 |
| 20 | Amberlyst 36 | 21.6 | 8.1 | 2.7 | 19.1 | 32 | 95 | 60 | 1.7 |
| 21 | idem | | | | 5.3 | 67 | 100 | 85 | 7.2 |
| 22 | Purolite MN500 | 5.4 | 4.1 | 1.3 | 19.4 | 53 | 92 | 38 | 0.4 |
| 23 | idem | | | | 5.5 | 70 | 100 | 85 | 1.7 |

[a]WHV: weight hourly velocity;
[b]Falc: furfuryl alcohol;
[c]EL: ethyl levulinate;
[d]DEE: di-ethylether.

What is claimed is:

1. A process for the conversion of furfuryl alcohol into levulinic acid or alkyl levulinate comprising contacting furfuryl alcohol and water or an alkyl alcohol with a porous heterogeneous catalyst comprising strong acid ion-exchange resin, wherein the catalyst has pores with an average pore diameter in the range of from 1 to 1000 nm.

2. A process according to claim 1, wherein the catalyst is a strong acid macro-reticular ion-exchange resin.

3. A process according to claim 1, wherein a liquid reaction mixture comprising furfuryl alcohol and water or alkyl alcohol is contacted with the catalyst.

4. A process according to claim 3, wherein the concentration of furfuryl alcohol in the liquid reaction mixture is at most 10 wt % based on the total weight of the liquid reaction mixture.

5. A process according to claim 3, wherein the molar ratio of water or alkyl alcohol and furfuryl alcohol in the liquid reaction mixture is in the range of from 1 to 100.

6. A process according to claim 1, wherein the catalyst comprises acidic sulphonic groups.

7. A process according to claim 1, wherein the catalyst has a specific surface area of at least 5 $m^2/g$.

8. A process according to claim 1, wherein the temperature at which the reactants are contacted with the catalyst is in the range of from 80 to 250° C.

9. A process for the conversion of furfuryl alcohol into alkyl levulinate according to claim 1, comprising contacting furfuryl alcohol and an alkyl alcohol with a porous heterogeneous acid catalyst.

10. A process according to claim 9, wherein the alkyl alcohol is an alkyl alcohol having at most 10 carbon atoms.

11. A process according to claim 9, wherein the alkyl alcohol is a primary alkyl alcohol having at most 10 carbon atoms.

12. A process according to claim 2, wherein a liquid reaction mixture comprising furfuryl alcohol and water or alkyl alcohol is contacted with the catalyst.

13. A process according to claim 3, wherein the concentration of furfuryl alcohol in the liquid reaction mixture is at most 2 wt % based on the total weight of the liquid reaction mixture.

14. A process according to claim 4, wherein the molar ratio of water or alkyl alcohol and furfuryl alcohol in the liquid reaction mixture is in the range of from 1 to 100.

15. A process according to claim 3, wherein the molar ratio of water or alkyl alcohol and furfuryl alcohol in the liquid reaction mixture is in the range of from 1.5 to 10.

16. A process according to claim 4, wherein the molar ratio of water or alkyl alcohol and furfuryl alcohol in the liquid reaction mixture is in the range of from 1.5 to 10.

17. A process according to claim 1, wherein the catalyst has a specific surface area of at least 20 m$^2$/g.

18. A process according to claim 1, wherein the temperature at which the reactants are contacted with the catalyst is in the range of from 100 to 220° C.

19. A process according to claim 9, wherein the alkyl alcohol is methanol, ethanol, 1-butanol, 1-pentanol, 2-ethylhexan-1-ol or a combination of two or more thereof.

20. A process according to claim 9, wherein the ion-exchange resin has a ratio of strong acidic groups at its surface and strong acidic groups inside its polymeric phase that is at least 3.0.

* * * * *